United States Patent

Yoshikawa et al.

(10) Patent No.: US 6,518,250 B2
(45) Date of Patent: Feb. 11, 2003

(54) AGENT FOR PREVENTING AND CURING HINDRANCE OF ISCHEMIC REPERFUSION

(75) Inventors: Toshikazu Yoshikawa, Uji; Hironobu Murase, Gifu; Norimasa Yoshida, Kyoto, all of (JP)

(73) Assignee: CCI Corporation (JP)

( * ) Notice: Subject to any disclaimer, the term of this patent is extended or adjusted under 35 U.S.C. 154(b) by 65 days.

(21) Appl. No.: 09/993,194

(22) Filed: Nov. 14, 2001

(65) Prior Publication Data

US 2002/0128211 A1 Sep. 12, 2002

Related U.S. Application Data

(63) Continuation of application No. 09/601,716, filed as application No. PCT/JP99/00007 on Jan. 5, 1999, now abandoned.

(30) Foreign Application Priority Data

Feb. 6, 1998 (JP) .......................................... 10-026264

(51) Int. Cl.$^7$ .............................................. A61K 31/70
(52) U.S. Cl. ............................ 514/25; 514/23; 514/27; 514/32; 514/53; 514/54; 514/824; 514/878; 514/925; 514/926
(58) Field of Search .............................. 514/23, 25, 27, 514/32, 53, 54, 824, 878, 925, 926

(56) References Cited

FOREIGN PATENT DOCUMENTS

JP          A-7-118287     *   7/1990

OTHER PUBLICATIONS

"Chemistry and Organisms", vol. 30, No. 3, pp. 184 and 185 (1992).*

"Journal of Japan Petrochemical Society", vol. 46, No. 10, p. 107 (1997).*

"J. Act. Oxyg. Free Rad.", vol. 1, No. 3, p. 316 (1990).*

"All about Anti–oxidant Substances", Toshiichi Yoshikawa, publisher Sentan Igakusha, first print edition, p. 270 (1998).*

\* cited by examiner

*Primary Examiner*—Frederick Krass
(74) *Attorney, Agent, or Firm*—Mathews, Collins, Shepherd & McKay, P.A.

(57) ABSTRACT

An agent for preventing and curing the hindrance of ischemic reperfusiton is disclosed which has as an active component thereof a chromanol glycoside represented by the following general formula:

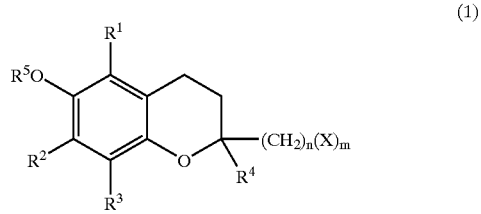

(1)

[wherein $R^1$, $R^2$, $R^3$, and $R^4$ independently denote a hydrogen atom or a lower alkyl group, $R^5$ denotes a hydrogen atom, a lower alkyl group, or a lower acyl group, X denotes a monosaccharide residue or an oligosaccharide residue which may have a lower alkyl group or a lower acyl group substituted for the hydrogen atom of the hydroxyl group of the saccharide residue, n denotes an integer of 0–6, and m denotes an integer of 1–6]. The agent, even in a small dosage, acts safely and effectively on the affected part and allows the hindrances of ischemic reperfusion induced in heart, stomach, small intestine, liver, spleen, kidney, brain, and skin, and the hindrance induced during the transplantation of an internal organ to be prevented and cured.

4 Claims, No Drawings

AGENT FOR PREVENTING AND CURING HINDRANCE OF ISCHEMIC REPERFUSION

This application is a continuation of U.S. Ser. No. 09/601,716, filed Sep. 22, 2000, now abondoned, which is a 371 of PCT/JP99/00007, filed Jan. 5, 1999.

TECHNICAL FIELD

This invention relates to a novel agent for preventing and curing the hindrance of ischemic reperfusion. More particularly, the invention relates to an agent having a water-soluble chromanol glycoside as an active component and used for preventing and curing the hindrance of ischemic reperfusion.

BACKGROUND ART

If the human cells and tissues are exposed to ischemic condition for long time, they suffer serious damage and eventually result in cell death. On the other hand, when a sudden oxygen load is exerted thereon by an ischemic reperfusion for a certain duration, they sustain further serious hindrance. Clinically, these hindrance of the ischemic reperfusion have been heretofore recognized as diseases to be observed during the transplantation of an internal organ or the reconstruction of the coronary blood flow for a myocardial infarct. In recent years, since the involvement of a free radical reaction in the histological hindrance due to the ischemic reperfusion in a feline intestine was pointed out (Granger, D. N. et al.: Superoxide radicals in feline intestinal ischemia. Gastroenterol. 22–29, 1981), the studies in this field have been widely disseminated and the involvement of active oxygen free radical in the hindrance of ischemic reperfusion in not only the small intestine but also the brain, heart, stomach, liver, kidney, and so on has been appearing in reports. Therefore, numerous studies have been being promoted with a view to seeking out ways of alleviating the relevant diseases by the administration of an exogenous radical eliminating agent. However, owing to various problems concerning the in vivo action and the field of reaction, however, all the radical eliminating agents are not capable of effectively restraining the histological hindrance due to the ischemic reperfusion (Hirofumi Kazumori et al.: Proposal of problems concerning the hindrance of reperfusion and free radicals, J. Act. Oxyg. FreeRad.: 757–766, 1991). This fact is self-evident from a present state that virtually no radical eliminating agent has been authorized as a drug.

The chromanol glycoside to be used in this invention is a known compound (the official gazette of JP-A-07-118,287). The chromanol glycoside is obtained by substituting an alcohol for the phytyl group at the 2 position of a chroman ring of α-tocopherol, which is a typical vitamin E and further binding a sugar thereto. It possesses high water solubility and excellent resistance to oxidation. The utilization of the chromanol glycoside for the prevention and the cure of the hindrance of the ischemic reperfusion, however, has not been known.

This invention has been initiated with a view to solving the problems entailed by the prior art mentioned above. An object of this invention is to provide a novel agent for preventing and curing hindrance of ischemic reperfusion, which agent effectively acts at a small dosage without entailing any side reaction and prevents various hindrance induced by the ischemic reperfusion or permits the condition of disease to be alleviated or eliminated.

Another object of this invention is to provide a novel agent for preventing and curing hindrance of ischemic reperfusion, which agent is capable of offering commendable resistance to oxidation and bringing effective repression and control of free radical reactions in the parts of various internal organs affected by the hindrance of ischemic reperfusion.

Still another object of this invention is to provide a novel agent for preventing and curing hindrance of ischemic reperfusion, which agent can be formulated as an aqueous pharmaceutical agent containing an active component at high concentration.

DISCLOSURE OF THE INVENTION

The present inventors have performed diligent studies one after another in search of an agent for preventing and curing hindrance of the ischemic reperfusion and, consequently, have discovered that the chromanol glycoside mentioned above is capable of dramatically preventing and curing morbid alterations of the hindrance of the ischemic reperfusion.

Specifically, this invention concerns an agent for preventing and curing the hindrance of the ischemic reperfusion, which agent has as an active component thereof a chromanol glycoside represented by the following general formula:

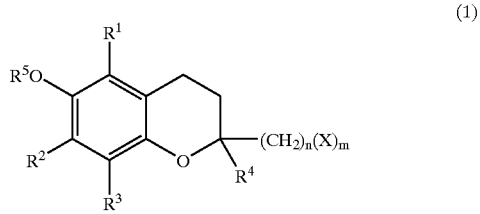

(1)

[wherein $R^1$, $R^2$, $R^3$, and $R^4$ independently denote a hydrogen atom or a lower alkyl group, $R^5$ denotes a hydrogen atom, a lower alkyl group, or a lower acyl group, X denotes a monosaccharide residue or an oligosaccharide residue which may have a lower alkyl group or a lower acyl group substituted for the hydrogen atom of the hydroxyl group of the saccharide residue, n denotes an integer of 0–6, and m denotes an integer of 1–6].

This invention also concerns the agent mentioned above, wherein said chromanol glycoside mentioned above is 2-(α-D-glucopyranosyl) methyl -2,5,7,8-tetramethylchroman-6-ol.

This invention further concerns the agent mentioned above, wherein said hindrance of ischemic reperfusion is a hindrance of small intestinal mucous membrane or a hindrance of cerebral ischemic reperfusion.

This invention also concerns an agent for preventing and curing the hindrance of the ischemic reperfusion which is an aqueous pharmaceutical agent.

BEST MODE OF EMBODYING THE INVENTION

The agent of this invention for preventing and curing the hindrance of ischemic reperfusion is characterized by having a chromanol glycoside represented by the general formula (1) mentioned above as an active component.

In the general formula (1) mentioned above, the lower alkyl groups of $R^1$, $R^2$, $R^3$, $R^4$ and $R^5$ are favorably to be lower alkyl groups of carbon atoms 1–8, preferably 1–6. As concrete examples of the lower alkyl groups, methyl group, ethyl group, propyl group, isopropyl group, butyl group, isobutyl group, pentyl group, isopentyl group, hexyl group, hyptyl group, and octyl group may be cited. Among other lower alkyl groups mentioned above, methyl group or ethyl group proves particularly advantageous. The lower acyl groups of $R^5$ are favorably to be lower acyl groups of 1–8, preferably 1–6, carbon atoms. As concrete examples of the lower acyl groups, formyl group, acetyl group, propionyl group, butylyl group, isobutylyl group, valeryl group, isovaleryl group, pivaloyl group, hexanoyl group, heptanoyl group, and octanoyl group may be cited. Among other lower acyl groups mentioned above, acetyl group, propionyl group, or butylyl group proves particularly advantageous. As concrete examples of the monosaccharide residues of X, sugar residues such as glycose, qalactose, fucose, xylose, mannose, rhamnose, fructose, arabinose, lyxose, ribose, allose, altrose, idose, talose, deoxyribose, 2-deoxyribose, quinovose, and abequose may be cited. As concrete examples of the oligosaccharide residues, such sugar residues as maltose, lactose, cellobiose, raffinose, xylobiose, and sucrose which are formed by the union of two to four such monosaccharides as mentioned above. Among other monosaccharide residues mentioned above, glucose, galactose, fucose, xylose, rhamnose, mannose, and fructose prove particularly advantageous. The hydrogen atom of the hydroxyl group in the saccharide residue of X may be substituted for a lower alkyl group, preferably a lower alkyl group of 1–8 carbon atoms, or for a lower acyl group, preferably a lower acyl group of 1–10 carbon atoms. Then, n denotes an integer of 0–6, preferably 1–4, and m denotes an integer of 1–6, preferably 1–3. As preferred examples of the chromanol glycoside represented by the general formula (1), 2-($\alpha$-D-glucopyranosyl)methyl-2,5,7,8-tetramethylchroman-6-ol, 2-($\beta$-D-galactopyranosyl) methyl-2,5,7,8-tetramethylchroman-6-ol, 2-($\beta$-L-fucopyranosyl)methyl-2,5,7,8-tetramethylchroman-6-ol, 2-($\alpha$-L-rhamnopyranosyl)-methyl-2,5,7,8-tetramethylchroman-6-ol, 2-($\beta$-D-xylopyranosyl)methyl-2,5,7,8-tetramethylchroman-6-cl, 2-($\beta$-D-glucopyranosyl)methyl-2,5,7,8-tetramethylchroman-6-ol, 2-($\beta$-D-fructofuranosyl)methyl-2,5,7,8-tetramethylchroman-6-ol, and 2-($\alpha$-D-mannopyranosyl)methyl-2,5,7,8-tetramethylchroman-6-ol may be cited.

The chromanol glycoside to be used in this invention is produced by an enzymatic reaction according to the method disclosed in the official gazette of JP-A-07-118,287, for example, by causing a 2-substituted alcohol represented by the following general formula (2);

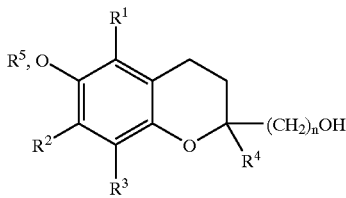

(2)

(wherein $R^1$, $R^2$, $R^3$, $R^4$, and $R^5$ and n have the same meanings as defined above) to react with an oligosaccharide, a soluble starch, starch, or cyclodextrin in the presence of an enzyme capable of catalyzing a corresponding transglycolytic action thereby causing a specific hydroxyl group of sugar to be bound specifically to the hydroxyl group at the 2 position of the 2-substituted alcohol (enzyme method).

The 2-substituted alcohol represented by the general formula (2) used as the raw material in the reaction mentioned above (hereinafter referred to simply as "2-substituted alcohol") is a known substance which can be obtained by the method disclosed in the official gazette of JP-B-01-43,755 or the official gazette of JP-B-01-49,135, etc. The 2-substituted alcohol which satisfies the general formula (2) by having a methyl group for each of $R^1$, $R^2$, $R^3$, and $R^4$, a hydrogen atom for $R^5$, and 1 for n, for example, can be easily obtained as by refluxing Tororox in diethyl ether in the presence of lithium aluminum hydride.

The enzyme which is used in the reaction mentioned above for the purpose of catalyzing the transglycolytic action is preferred to be properly selected to suit the kind of a sugar to be used as follows.

(1) In binding a glucose residue to the 2-substituted alcohol by the $\alpha$-bonding:

(a) The maltooligosaccharides of the range of maltose through maltotetrose are preferred to be acted on by an $\alpha$-glucosidase, EC 3.2.1.20. The $\alpha$-glucosidase to be used herein does not need to be discriminated on account of its origin. As concrete examples of the $\alpha$-glucosidase, the $\alpha$-glucosidase from the microorganism of genus Saccharomyces sp. made by TOYOBO Co., Ltd., the $\alpha$-glucosidase from the microorganism of genus *Saccharomyces cerevisiae* made by Oriental Yeast Industry Co., Ltd., the $\alpha$-glucosidase from the microorganism of genus *Aspergillus niger* made by Amano Pharmaceutical Co., Ltd., the $\alpha$-glucosidase from the microorganism of genus Saccharomyces sp. made by wako Pure Chemical Industries Ltd., the $\alpha$-glucosidase from the microorganism of Bakers yeast made by SIGMA Corp., and the $\alpha$-glucosidase from the microorganism of genus Bacillus may be cited.

(b) The soluble starch or starch is preferred to be acted on by 4-$\alpha$-D-glucanotransferase, EC2.4.1.25.

(2) In binding a glucose residue or a maltooligosaccharide residue to the 2-substituted alcohol by the $\alpha$-bonding:

The maltoligosaccharide, soluble starch, starch, or cyclodextrin ($\alpha$, $\beta$, $\gamma$), etc. is preferred to be acted on by cyclodextrin glucanotransferase, EC2.4.1.19. As typical examples of the cyclodextrin glucanotransferase, the cyclodextrin glucanotransferase from the microorganism of genus *Bacillus macerans* made by Amano Pharmaceutical Co., Ltd., the cyclodextrin glucanotransferase from the microorganism of genus *Bacillus stearothermophilus* made by Hayashi Genseibutsu Kagaku Kenkyusho, Ltd., and the cyclodextrin glucanotransferases from the microorganisms of *Bacillus megaterium* and *Batillus circulans* ATCC 9995 may be cited.

(3) In binding a glucose residue to the 2-substituted alcohol by the $\beta$-bonding:

(a) Such oligosaccharide as cellobiose, curdlan, or laminaran, for example, which are formed by the $\beta$-bonding is preferred to be acted on by $\beta$-glucosidase, EC 3.2.1.21.

(b) Cellobiose in the presence of phosphoric acid is preferred to be acted on by cellobiose phosphorylase, EC2.4.1.20.

(4) In binding a galactose residue to the 2-substituted alcohol by the $\alpha$-bonding:

(a) Melibiose or raffinose, for example, is preferred to be acted on by $\alpha$-galactosidase, EC3.2.1.22.

(5) In binding a galactose residue to the 2-substituted alcohol by the $\beta$-bonding:

(a) Lactose, for example, is preferred to be acted on by $\beta$-galactosidase, EC3.2.1.23.

(b) Arabinogalactan, for example, is preferred to be acted on by endo-1,4-$\beta$-galactose, EC3.2.1.89.

(6) In binding a fructose residue to the 2-substituted alcohol by the β-bonding:
   (a) Sucrose, raffinose, or melibiose, for example, is preferred to be acted on by Levansucrase, EC2.4.1.10.
   (b) Sucrose, for example, is preferred to be acted on by β-fructofuranosidase, EC3.2.1.26.
   (c) Inulin, for example, is preferred to be acted on by inulin fructotransferase, EC2.4.1.93.

The conditions for the reaction mentioned above are variable with the kind of a chromanol glycosidase and the kind of an enzyme to be used. For example, when the chromanol glycoside which satisfies the general formula (1) by having 1 for m is to be synthesized by using an α-glucosidase, the 2-substituted alcohol is preferred to be dissolved in the sugar solution. Accordingly, it is preffered to add an organic solvent to the solution. As concrete examples of the organic solvent, dimethylsulfoxide, N,N-dimethylformamide, methanol, ethanol, acetone, and acetonitrile may be cited. Among other organic solvents, dimethylsulfoxide and N,N-dimethylformamide prove particularly suitable in consideration of the ability to improve the transfer activity of the α-glucosidase. The concentration of the added organic solvent is in the range of 1–50 (v/v) %. In view of the efficiency of the reaction, it is preferred to be in the range of 5–35 (v/v) %.

The 2-substituted alcohol is preferred to have a saturated concentration or a concentration approximating closely thereto in the reaction solution. The kind of sugar to be used is preferred to be sugar having low molecular weight, in the rang of approximately from maltose through maltotetraose. The maltose is a preferred choice. The concentration of the sugar is in the range of 1–70 (w/v) %, preferably 30–60 (w/v) %. The pH is in the range of 4.5–7.5, preferably 5.0–6.5. The reaction temperature is in the range of 10–70° C., preferably 30–60° C. The reaction time is in the range of 1–40 hours, preferably 2–24 hours. Needless to mention, these conditions are affected by the amount of the enzyme to be used, for example. After the reaction is completed, the chromanol glycoside aimed at is obtained at high purity by treating the reaction solution by the column chromatography using XAD (produced by Japan Organo Co., Ltd.) as a carrier.

When the chromanol glycoside satisfying the general formula (1) by having 1 for m is to be synthesized by using cyclodextrin glucanotransferase, the reaction condition is preferable that the 2-substituted alcohol is dissolved in the sugar solution. It is preferable to add organic solvent, such as dimethylsulfoxide, N,N-dimethyl formamide, methanol, ethanol, acetone, acetonirtle, etc. The concentration of the added organic solvent is in the range of 1–50 (v/v) %. In view of the efficiency of the reaction, this concentration is preferred to be in the range of 5–35 (v/v) %. The 2-substituted alcohol is preferred to have a saturated concentration or a concentration approximating closely thereto in the reaction solution.

As preferred concrete examples of the sugar to be used in the reaction mentioned above, maltoligosaccharide having polymerization degree exceeding that of maltotriose, soluble starch, starch, and cyclodextrin (α, β, γ) may be cited. The concentration of the sugar is in the range of 1–70 (w/v) %, preferably 5–50 (w/v) %. The pH is in the range of 4.5–8.5, preferably 5.0–7.5. The reaction temperature is in the range of 10–70° C., preferably 30–60° C. The reaction time is in the range of 1–60 hours, preferably 2–50 hours. These conditions, however, are affected by the amount of the emzyme to be used. The chromanol glycoside which has been obtained by the reaction described above forms a mixture satisfying the general formula (1) by having approximately 1 through 8 for m. Then, by treating this mixture with glucoamylase (EC3.2.1.3), the chromanol glycoside satisfying the general formula (1) by having 1 for m can be obtained exclusively. In this case, the reaction temperature is in the range of 20–70° C., preferably 30–60° C. and the reaction time is in the range of 0.1–40 hours, preferably 1–24 hours. However, these conditions are affected by the amount of the enzyme to be used. Then, by subjecting the solution remaining after the treatment with the glucoamylase mentioned above to column chromatography using XAD (made by Japan Organo Co., Ltd.) as a carrier, the chromanol glycoside satisfying the general formula (1) by having 1 for m is obtained at high purity.

The chromanol glycoside satisfying the general formula (1) by having 1 or 2 for m is exclusively obtained by causing the chroanol glycoside in the form of a mixture satisfying the general formula (1) of aporoximately 1 through 8 for m obtained by cyclodextrin glucanotransferase to be acted on by β-amylase (EC3.2.1.2). In this case, the reaction temperature is in the range of 20–70° C., preferably 30–60° C. and the reaction time is in the range of 0.1–40 hours, preferably 1–24 hours. These conditions however, are affected by the amount of the enzyme to be used. When the solution remaining after the treatment with the β-amylase is treated by the column chromatography using the XAD (made by Japan organo Co., Ltd.) as a carrier, the chromanol glycoside satisfying the general formula (1) by having 2 form is obtained at high purity and, at the same time, the chromanol glycoside satisfying the general formula (1) by having 1 for m is obtained.

In obtaining the chromanol glycoside satisfying the general formula (1) by having not less than 3 for m, the chromanol glycoside of high purity can be obtained for each value of m by preparing chromanol glycoside in the form of a mixture satisfying the general formula (1) having approximately 1 through 8 for m with cyclodextrin glucanotransferase and treating this chromanol glycoside, for example, by the fractionation chromatography using HPCL, etc.

The mode of embodiment, as described above, consists in binding a glucose residue or a maltoligosaccharide residue as a sugar residue to the 2-substituted alcohol. The mode of embodiment also can be likewise used advantageously in this invention, in which a galactose residue, a β-glucose residue, a mannose residue, or a fructose residue as a sugar residue is bound to the 2-substituted alcohol. In this mode, the chromanol glycoside aimed at is obtained at high purity by following the same procedure as the mode of embodiment mentioned above while suitably selecting a proper enzyme among the enzymes described in the foregoing paragraph concerning the enzymes capable of catalyzing the transglycolysis mentioned above (the official gazette of JP-A-09-249,688, Japanese Patent Application No. 9-176,174).

The chromanol glycoside to be used in this invention can be produced alternatively by preparing the 2-substituted alcohol mentioned above in a form having the hydroxyl group at the 6 position thereof protected with a protecting group (hereinafter referred to as "sugar acceptor") and a sugar derivative having a leaving group introduced to the anomer position and having the other hydroxyl group protected with a protecting group (hereinafter referred to as "sugar donor") and subjecting the sugar acceptor and the sugar donor to a condensing reaction in accordance with the method disclosed in the official gazette of Japanese Patent Application No. 10-75,599 (organic synthesis method).

As concrete examples of the protecting group for protecting the hydroxyl group at the 6 position of the sugar acceptor to be used in the reaction mentioned above, acetyl group, benzoyl group, pivaloyl group, chloroacetyl group, levulinoyl group, benzyl group, p-methoxybenzyl group, allyl group, t-butyldimethylsilyl group, t-butyldiphenylsilyl group, trimethylsilyl group, and trityl group may be cited. Among other protecting groups mentioned above, acetyl group and benzoyl group prove particularly advantageous.

As concrete examples of the leaving group introduced to the anomer position of the sugar donor to be used in the reaction mentioned above, halogen atoms such as chlorine, bromine, and fluorine, sulfur compounds such as thiomethyl group, thioethyl group, and thiophenyl group, and trichloroacetoimide group may becited. Among other leaving groups mentioned above, bromine, chlorine, thiomethyl group, thioethyl group, thioplhenyl group, and trichloroacetoimide group prove particularly advantageous. As concrete examples of the protecting group for protecting the hydroxyl group at a position other than the anomer position, acyl type protecting groups such as acetyl group, benzoyl group, pivaloyl group, chloroacetyl group, and levulinoyl group and ether type protecting groups such as benzyl group, p-methoxybenzyl group, allyl group, t-butyldimethylsilyl group, t-butyldiphenylsilyl group, trimethylsilyl group, and trityl group may be cited. Among other protecting groups mentioned above, acyl type protecting groups, especially acetyl group prove particularly advantageous.

The sugar donor can be easily prepared by introducing protecting groups to all the hydroxyl groups of a given sugar and then substituting the protecting group at the anomer position for a leaving group in accordance with the known method.

To illustrate the condensing reaction of the sugar acceptor and the sugar donor, the first step is to dissolve the sugar acceptor and the sugar donor in a nonpolar solvent. The amounts of the sugar acceptor and the sugar donor to be charged are expected to be such that the molar ratio of the sugar donor to the sugar acceptor fall in the range of 1.0–1.5, preferably 1.1–1.3. As concrete examples of the nonpolar solvent, methylene chloride and benzenemay becited.

Then, the condensing reaction of the sugar donor and the sugar acceptor is carried out under an anhydrous condition in the presence of an activating agent. As concrete examples of the activating agent, boron trifluoride ether complex, silver perchlorate, silver trifluorqmethane sulfonate, mercury bromide, mercury cyanide, N-iodosuccinicimide-trifluoromethanesulfonate, dimethylmethylthiosulfonium triflate, and p-toluenesulfonic acid may be cited. Particularly when bromine is used as a leaving group for the sugar derivative, it is commendable to use such a heavy metal salt as silver perchlorate. The reaction temperature is in the range of 5–30° C., preferably 10–25° C., and the reaction time is in the range of 12–48 hours, preferably 20–30 hours.

Subsequently, 2-(β-L-fucopyranosyl)methyl-2,5,7,8-tetramethylchroman-6-ol, 2-(α-L-rhamnopyrasyl)methyl-2,5,7,8-tetramethylchroman-6-ol, 2-(β-D-xylopyranosyl) methyl-2,5,7,8-tetramethylchroman-6-ol, etc. can be obtained by purifying the consequently obtained reaction product, for example, by the silica gel column chromatography thereby depriving the rotecting group of its function with sodium hydroxide and a methanolic hydrochloric acid, for example (JP-A-10-75,599).

The chromanol glycoside which is obtained by the enzyme technique or the technique of organic synthesis generally is an amphipatic molecule possessing exceptionally high solubility in water (about 100 g/100 ml) and abounding in solubility oil (octanol/water type distribution coefficient >3). That is, the chromanol glycoside according to this invention may well be called a water-soluble vitamin E endowed with high affinity for oil. Unlike the conventional vitamin E derivative which is insoluble or poor soluble in water, the chromanol glycoside according to the present invention retains high affinity for oil even when it is used as dissolved in water and, therefore, possesses an ability to permeate cell membranes and further enter cell interiors, fortifies the in vivo protecting system in resisting oxidation, prevents the hindrance of ischemic reperfusion by effectively repressing and controlling the active oxygen and the free radical in the parts affected by the hindrance of ischemic reperfusion, or brings a prominent improvement capable of healing the condition of the disease due to the hindrance of the ischemic reperfusion. Further, the chromanol glycoside which is obtained by the reaction mentioned above extremely excels tocopherol, Tororox, or 2-substituted alcohol in terms of thermal stability and pH stability.

The agent of this invention for preventing and curing the hindrance of ischemic reperfusion can be orally or otherwise administered to patients in the form of a composition having the chromanol glycoside mentioned above formulated with pharmaceutically allowable carriers or dissolved or suspended in a pharmaceutically allowable solvent.

For the purpose of applying the agent to oral administration, the chromanol glycoside mentioned above is suitably mixed with proper additives such as, for example, milk sugar, sucrose, mannitol, ccrn starch, synthetic or natural rubber, and crystalline cellulose, binding agents such as, for example, starch, cellulose derivatives, gum arabic, gelatine, and polyvinyl pyrrolidone, decaying agents such as, for example, carboxymethyl cellulose calcium, carboxymethyl cellulose sodium, starch, corn starch, and sodium alginate, glossing agents such as, for example, talc, magnesium stearate, and sodium stearate, and fillers or diluents such as, for example, calcium carbonate, sodium carbonate, calcium phosphate, and sodium phosphate and formulated as solid pharmaceutical agents as tablets, dust (powder), pills, and granules. It may be otherwise encapsulated with hard or soft gelatine capsules. These solid pharmaceutical agents may be furnished with an enteric coating using any of the coating bases such as, for example, hydroxypropylmethyl cellulose phthalate, hydroxypropylmetyl cellulose acetate succinate, cellulose acetate phthalate, and methacrylate copolymers. Further, the chromanol glycoside mentioned above may be formulated as liquid preparations such as syrup agents and elixir agents by dissolving this glycoside in an inert dilutent popularly used in purified water and, as occasion demands, suitably adding to the solution a wetting agent, an emulsifier, a dispersion auxiliary, a surfactant, an edulcorant, a flavor, an aromatic substance, or the like.

For the administration not via the mouth of the agent of this invention for preventing and curing the hindrance of ischemic reperfusion, the chromanol glycoside mentioned above may be formulated in the form of a sterilized aqueous solution, a non-aqueous solution, a suspension, a ribosome, or an emulsion, preferably an injection grade solution or a spray grade sterilized aqueous solution, as suitably combined with purified water, a proper buffer solution such as a phosphate buffer solution, a physiological common salt solution, a physiological salt solution such as a Ringer's solution or a Locke's solution, ethanol, glycerin, and a popular surfactant. Such a preparation may be administered intravenously, hypodermically, intramuscularly, intra-abdominally, intestinally, and intrabronchially. The liquid preparation in this case is preferred to have a physiological pH, preferably a pH in the range of 6–8. Further, the agent of this invention for preventing and curing the hindrance of ischemic reperfusion may be administered as embedded by a pellet or as prepared in the form of a suppository using a suppository basis.

In the preparations and the modes of administration mentioned above, those which are appropriate for a given patient are selected by a physician in charge.

Though the concentration in which the chromanol glycoside is contained in the agent of this invention for preventing and curing the hindrance of ischemic reperfusion is varied by the mode of administration, the kind of disease, the degree of seriousness of disease, and the dosage aimed at, it is generally in the range of 0.1–10 wt. %, preferably 1–90 wt. %, based on the total weight of the raw materials. Particularly when the preparation of this invention is orally administered, the concentration is in the range of 1–100 wt. %, preferably 5–90 wt. %, based on the total weight of the raw materials. In the case of the administration parenterally, the concentration is in the range of 0.1–90 volume %, preferably 1–80 volume %, based on the total volume of the raw materials. In this case, if the concentration of the chromanol glycoside exceeds the upper limit of the range mentioned above, the excess will not bring a proportionate addition to the effect in alleviation of the condition of disease. Conversely, if this concentration is less than the lower limit of the range, it will be at a disadvantage in preventing the alleviation of the condition of disease from being fully achieved.

The aforementioned dosage of the agent of this invention for preventing and curing the hindrance of ischemic reperfusion is variable with the age, body weight, and symptom of a relevant patient, the mode and method of administration aimed at, the effect of treatment, and the duration of treatment. The accurate dosage is to be decided by a physician. Generally when the preparation is orally administered, the amount of the preparation as reduced to the dosage of the chromanol glycosideis in the range of 0.1–10000 mg/kg of body weight/day, one through three times daily. In this case, when the daily oral dosage is large, the preparation may be administered at a rate of a plurality of tablets in one dosage. When the agent of this invention for preventing and curing the hindrance of ischemic reperfusion is administered parenterally, the preparation is administered once wholly or one or three times as split daily in such an amount that the dosage of chromanol glycoside as reduced to the dosage of the chromanol glycoside will be in the range of 0.01–1000 mg/kg of body weight/day.

The agent of this invention for preventing and curing the hindrance of ischemic reperfusion can be utilized for preventing and curing the hindrances caused in various sites such as, for example, heart, stomach, small intestine, liver, spleen, kidney, brain, eyeball, and skin by ischemic reperfusion and various hindrances caused during the transplantation of an internal organ. To be specific, the hindrances mentioned above include such hindrances as hindrances of cerebral ischemic reperfusion and cardiac muscular ischemic reperfusion, the hindrances which arise during the reconstruction of ranial blood circulation in various infarctions such as cerebral infarction, myocardial infarction, and pulmonary infarction, during the formation of cardiopulmonary bypass, and during the transplantation of an internal organ, and the hindrances of microcirculation in the mucous membrane of the digestive system and the surface of the eyeball caused by stress, for example. The hindrances of the cerebral ischemic reperfusion mentioned above include ischemic cerebral edema and likes and the hindrances of the myocardial ischemic reperfusion include ventricular arrhythmia observed before and after elimination of coronary spasm and resumption of blood circulation by solution of thrombus, heart rupture due to infarct tissue internal hemorrhage, and imperfect recuperation of the heart function and stunned myocardium after the fallaway of mechanical heart-lung encountered during the surgical operation of the heart.

Pharmacologic Test

The pharmacological effect of the agent of this invention for preventing and curing the hindrance of ischemic reperfusion will be described more specifically below with reference to pharmaceutical tests using animals.

In each pharmacological test, the 2-(α-D-glucopyranosyl) methyl-2,5,7,8-tetramethylchroman-6-ol (TMG) represented by the following formula (3) which was produced by the method described in Example 1 cited in the official gazette of JP-A-07-118,287 was used as a chromanol glycoside.

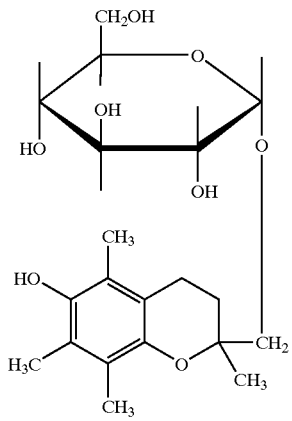

(3)

[Repressing Effect of Morbid Alteration with Model of Hindrance of Small Intestinal Ischemic Reperfusion]

A model of hindrance of small intestinal ischemic reperfusion was produced in a rat by ligating the celiac arteria and at the same time blocking the superior mesenteric artery with a clip to suspend the bloodstream therethrough for 30 minutes, then relieving them of the respective obstructions and allowing reperfusion to last for 60 minutes, and thereafter rating the hindrance of mucous membrane in the small intestine. When a morbid alteration occurred in the mucous membrane of the small intestine, hemorrhage in the small intestinal lumen, protein transudation, and increase of the thiobarbituric acid (TBA) reaction substance (index of lipid peroxidation) in the mucous membrane were recognized. With such substances as the index, the model was tested for the effect of the chromanol glycoside in suppressing the morbid alteration of the hindrance of ischemic reperfusion.

SD type male rats (body weights 180–200 g) divided into groups of six heads were made to keep 18 hours' fasting before they were put to use in the test. They were subjected to median ventrotomy under anesthesia with urethane (1000 mg/kg) and caused to assume a state of ischemia by ligating the celiac arteria and then blocked the superior mesenteric artery at the root with a clip. After the elapse of 30 minutes thence, a TMG preparation obtained by thoroughly dissolving TMG at a concentration of 0.8 mg/ml in physiological common salt solution was administered to the rats through intravenous injection at a rate of 4 mg/kg of body weight, and then reperfusion was started by removing the clip. After 60 minutes of the reperfusion, the rats were sacrificed by releasing blood from the aorta. The small intestines were excised from the sacrificed rats and the hemoglobin translated from the small intestinal lumen, the transudated protein, and the TBA reaction substance in the small intestinal mucous membrane were determined quantitatively.

The results consequently obtained are shown in Table 1 together with the results obtained of the normal group of rats which had not undergone the treatment of ischemic reperfusion and the administration of TMG preparation and the results obtained of the control group of rats which had undergone the administration by intravenous injection of physiological common salt solution in the same amount in the place of the TMG preparation after the ischemia and before the reperfusion. The items of the rating mentioned above were determined by the following methods.

(1) Method for measurement of hemoglobin transudated from the small intestinal lumen and transudated protein As the index of the hindrance of the small intestinal mucous membrane by ischemic reperfusion, the amount of the hemoglobin and the amount of protein transudated into the small intestinal lumen were measured. A 30-cm adoral portion of the small intestine was excised from a site at a distance of 5 cm from the terminal end of the ileum, the interior of the small intestinal lumen was washed from the adoral side with 10 ml of a cold physiological common salt solution, and the washing recovered consequently was put to use for the measurement. The amount of the hemoglobin transudated was measured by the cyanmethemoglobin technique (Cannan, R. K.: Am. J. Clin. Path., 44, 207–210, 1965) using a hemoglobin measuring kit (made by Wako Pure Chemical Industries, Ltd. And sold under the trademark designation of "Hemoglobin Test Wako"). Specifically, 0.2 ml of the intestine washing solution was intimately mixed with 5 ml of a coloring reagent (0.78 mM potassium cyanide+0.61 mM potassium ferricyanide). The produced mixture was left standing at room temperature for 5 minutes and then tested for absorbance with a spectrophotometer (made by Jasco Engineering K.K. and sold under the trademark designation of "JASCO Ubest-30, UV/VIS Spectrophotometer") at a wave length of 540 nm. The hemoglobin content of the washing was calculated from the calibration curve obtained in advance with the cyanmethemoglobin standard solution (18 g of hemoglobin/dl+3.1 mM potassium cyanide+0.61 mM potassium ferricyanide) and was reported at the amount of hemoglobin per unit length of the small intestine. The amount of the protein transudated was measured by the Lowry technique (Lowry, O. H.: J. Biol. Chem., 193, 265–275, 1951) using a protein measuring kit (made by Sigma Chemical Co., Ltd.).

(2) Method for measurement of TBA reaction substance in small intestinal mucous membrane This measurement was carried out by the Ohkawa technique (Ohkawa, H.: Anal. Biochem., 95, 351–358, 1979). The adoral 10-cm portion of the small intestine was excised from the site at a distance of 5 cm from the terminal end of the ileum, cut open in the direction of major axis, and stripped of the mucous membrane with the aid of two slide glasses. The membrane was diluted to 10 times its own weight (wt. %) with an aqueous 10 mM phosphate buffer-30 mM potassium chloride solution as homogenized (by means of a homogenizer fitted with a Pyrex homogenizer grade glass 10 ml in volume, made by Iuchi Seiei Do K.K., and operated at 1000 rpm). The portion, 0.2 ml, of the homogenate, and 0.6 ml of distilled water and 0.2 ml of an aqueous 8.1% sodium disulfate solution added thereto, and 1.5 ml of a 20% phosphate buffer solution of pH 3.5, 1.5 ml of 0.8% TBA, and 40 $\mu$l of 1% BTH further added thereto were heated altogether in an oil bath (made by Taitekku K.K. and sold under the trademark designation of "OH-50P") at 95° C. for one hour and then cooled for 10 minutes. The produced mixture and 1.0 ml of distilled water and 5.0 ml of butanol pyridine (butanol:pyridine=15:1, v/v) added thereto were stirred and then centrifuged (1500 g, 10 minutes) at room temperature. The supernatant consequently obtained was tested for absorbance by means of a spectrophotometer (made by Jasco Engineering K.K. and sold under the trademark designation of "JASCO Ubset-30, UV/VIS Spectrophtometer) at a wave length of 535 nm. From the blank using 0.8 ml of distilled water and the standard using 0.3 ml of distilled water and 0.5 ml of TEP respectively in the place of 0.2 ml of the homogenate of small intestinal mucous membrane and 0.6 ml of distilled water, a calibration curve was obtained. The content of the TBA reaction substance in a given sample was calculated with reference to this calibration curve.

TABLE 1

|  | Hemoglobin transudated in small intestinal lumen (mg/cm) | Protein transudated in small intestinal lumen ($\mu$g/cm) | TBA reaction substance in small intestinal mucous membrane (nmol/g on wet basis) |
|---|---|---|---|
| Normal group | 0.5 ± 0.4 | 0.3 ± 0.1 | 57.1 ± 9.3 |
| Control group | 3.4 ± 1.5 | 1.6 ± 0.3 | 285.6 ± 105.7 |
| TMB administration group (4 mg/kg of bodyweight), i.v. | 0.4 ± 0.3** | 0.5 ± 0.1** | 112.8 ± 33.6* |

*Presence of significant error relative to control (P < 0.05)
**Presence of significant error relative to control (P < 0.01)

The results represent averages±standard errors.

The qualification of significant differences was verified by the one-dimensional dispersion analysis. The differences consequently found as significant were subjected to Scheffe's multiple verification.

It is clearly noted from Table 1 that the model of hindrance of ischemic reperfusion (control group) showed discernible increases in hemorrhage and protein transudation in the small intestinal lumen and in the TBA reaction substance in the mucous membrane and the TMG administration group showed significant repressions in these values. This fact indicates that the agent of this invention for preventing and curing the hindrance in ischemic reperfusion brought prominent repression of the hindrance of small intestinal mucous membrane induced by the iscmetic reperfusion.

[Effect of Repressing Morbid Alteration by Model of Hindrance in Cerebral Ischemic Reperfusion]

A model rat for the hindrance of cerebral ischemic reperfusion was produced by using a four blood vessel occlusion model rat (Cranial Nerve, Vol. 47, pp. 369–375, 1995) as the model of the prosencephalon ischemic reperfusion and performing on the rat the cerebral ischemia for five minutes and then continuing the reperfusion for 120 minutes. As a result of the ischemic reperfusion, the cerebral edema, i.e. a morbid state inducing accumulation or increase of the abnormal water content, was observed in the mass of the brain intracellularly or extracellularly or both occasionally. The same model was used, with the cerebral edema as the index, to study the effect of the chromanol glycoside in repressing the morbid alteration of the hindrance of cerebral ischemic reperfusion.

Wister type male rats (body weights 250–300 g) were used for the experiment as sorted into groups of 6 heads. The anesthesia, when the occlusion of the vertebral artery was elected, was effected by intraperitoneal administration injecting chloral hydrate(360 mg/kg). During the experiment, the body temperature of each rat was maintained at 37° C. as rectum temperature by means of a warm mat and a warm rap.

Each of the rats was laid in the prone position, fixed by the head on a rat fixing device, and cut open in a length of about 2 cm along the median line on the posterior region of the neck. At this point, the rectus capitis posterior on the opposite sides were peeled at the position of the second cervical vertebra with the aid of a microscope (made by Nagashima Medical Instrument Co., Ltd., Japan) and the opposite vertebral arteries were sought out in the occiput recti, peeled respectively from the connecting tissue, and exposed. With using a microsurgery grade bipolar coagulator, the opposite vertebral arteries were selectively electrocoagulated at the position of the second cervical vertebra. Further, the vertebral arteries could be infallibly occluded by cutting the coagulated part with microsurgery grade scissors and electrocoagulating the section. The treatment of the vertebral arteries was completed by suturing the ruptured skin with a silk thread. Then, the rat was set on the dorsal position and cut open longitudinally in a length of about 2 cm along the median line in the anterior region of the neck. Thereafter, the common carotid arteries on the opposite sides were exposed and peeled under the same microscope and they were stowed in the cut part by dint of a silk thread hooked thereon and the cut part was closed with a surgical staple. On the day following the surgical experiment, the surgical staple was removed from the cut anterior part of the neck, the silk thread stowed in the cut part was slightly pulled up, and the opposite common carotid arteries were closed laterally toward each other by the use of a Sugita's clip (No. 52) for cerebral aneurism to form a four blood vessel occlusion model.

The prosencephalon ischemia was imparted to the rat by continuing the occlusion of the opposite common carotid arteries for five minutes and, immediately before the start of the ischemic reperfusion, the TMG preparation obtained in advance by thoroughly dissolving TMG in physiological common salt solution at a concentration of 1.5 mg/ml was administered thereto by intravenous injection at a dose of 4 mg/kg of body weight. The reperfusion was started by removing the clip from the common carotid arteries. After the reperfusion had lasted for 120 minutes, the rat was immediately decapitated and the opposite cerebral hemispheres were promptly collected and weighed wet. Then, the cerebral hemispheres were dried in a drier at 100° C. for 48 hours and weighed dry. The difference of the weight before drying was found as the water content. Then, the ratio of the water content relative to the wet weight of the brain (ratio of the brain water content) was calculated.

The results consequently obtained are shown in Table 2 in conjunction with the results obtained of the control group in which the physiological common salt solution was administered in the same dose by intravenous injection immediately before the start of the ischemic reperfusion in the place of the TMG preparation.

TABLE 2

| | Ratio of water content to brain (%) |
|---|---|
| Control group | 78.66 ± 0.51 |
| TMG administration group (4 mg/kg of body weight) | 78.05 ± 0.28* |

*Presence of a significant error relative to the control ($P < 0.05$).

The results represent averages±standard deviations.

Significant effors were varified by the student t-test.

It is clearly noted from Table 6 that the TMG administration group showed significant repression of the ratio of water content to brain.

Test for Acute Toxicity

The agent of this invention for preventing and curing the cerebral edema due to the hindrances in the blood vessel was tested for acute toxicity with the view to confirming the safety of the use of the agent. The ICR type mice 4 to 5 weeks old were used in the test as sorted into groups of three heads. As the chromanol glycoside, the same TMG as mentioned above was suspended in an aqueous 5% gum arabic solution and the suspension wad orally administered to the rats at a rate of 500 mg/kg as reduced to TMG. The rats thus treated were placed under observation for one week. In this case, to the rats of the control group, an aqueous 5% gum arabic solution was administered orally at a rate of 0.3 ml. None of the mice of the groups to which the preparations were administered experienced death.

EXAMPLES OF PREPARATION

Example 1 of Preparation

A powder was obtained by mixing 100 g of TMG, 800 g of milk sugar, and 100 g of corn startch with a blender.

Example 2 of preparation

A granular agent was obtained by mixing 100 g of TMG, 450 g of milk sugar, and 100 g of hydroxypropyl cellulose of a low degree of substitution, kneading the resultant mixture with 350 g of an aqueous 10% hydroxypropyl cellulose solution, granulating the produced blend with an extrusion pelletizer, and drying the granules consequently formed.

Example 3 of Preparation

Tablets were obtained by mixing 100 g of TMG, 550 g of milksugar, 215 g of corn starch, 130 g of crystalline cellulose, and 5 g of magnesium stearate in a blender, and molding the produced blend with a tableting machine.

Example 4 of Preparation

A capsuled agent was obtained by mixing 10 g of TMG, 110 g of milk sugar, 58 g of corn starch, and 2 g of magnesium stearate in a V-shaped mixing machine and filling the capsules, No. 3, each with 180 mg of the resultant mixture.

Example 5 of Preparation

An injection agent was obtained by dissolving 200 mg of TMG and 100 mg of glucose in 1 ml of purified water, filtering the solution, dispensing the filtrate among 2-ml ampoules, sealing the ampoules, and sterilizing the filled ampoules.

Industrial Utilizability

Since the agent of this invention for preventing and curing the hindrance of ischemic reperfusion has a chromanol glycoside as an active component as described above, it is capable of reinforcing the in vivo system for resisting oxidation, allowing effective repression and control of active oxygen and free radicals in the part affected by the hindrance of ischemic reperfusion, conspicuously repressing a morbid alteration in the hindrance of ischemic reperfusion, and producing a marked improvement in eliminating the morbid state.

Further, since the agent of this invention uses as an active component a chromanol glycoside possessing high water solubility, it can be used as solid preparations and formulated as water preparations containing the active component at high concentrations. These preparations, even at a small dosage, function effectively on the affected part and prevent and cure the hindrance of ischemic reperfusion and, at the same time, warrant very safe use because it entails no side effect.

The agent of this invention for preventing and curing the hindrance of ischemic reperfusion can be utilized for preventing and curing the hindrances induced in various parts such as heart, stomach, small intestine, liver, spleen, kidney, brain, eyeball, and skin by the ischemic reperfusion and the hindrances incurred during the transplantation of internal organs.

What is claimed is:

1. A method for protecting cells and tissues from ischemic reperfusion damage, or for treating said damage, comprising a step of administrating to a person in need thereof an effective amount of a composition comprising an agent for protecting cells and tissues from ischemic reperfusion damage having as an active ingredient thereof a chromanol glycoside represented by the following general formula (1):

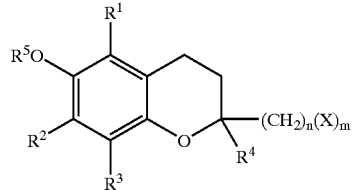

(1)

wherein $R^1$, $R^2$, $R^3$, and $R^4$ independently denote a hydrogen atom or a lower alkyl group, $R^5$ denotes a hydrogen atom, a lower alkyl group, or a lower acyl group, X denotes a monosaccharide residue or an oligosaccharide residue which may have a lower alkyl group or a lower acyl group substituted for the hydrogen atom of a hydroxyl group of said saccharide residue, n denotes an integer of 0–6, and m denotes an integer of 1–6.

2. A method according to claim 1, wherein said chromanol glycoside is 2-(α-D-glucopyranosyl) methyl-2,5,7,8-tetramethyl chroman-6-ol.

3. A method according to claim 1 wherein said ischemic reperfusion damage is small intestinal mucous membrane damage or cerebral ischemic reperfusion damage.

4. A method according to claim 1 wherein said composition is aqueous.

* * * * *